(12) United States Patent
Voelkl

(10) Patent No.: US 8,112,857 B2
(45) Date of Patent: Feb. 14, 2012

(54) STENT CRIMPING DEVICE

(75) Inventor: Claus Voelkl, Grosselfingen (DE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 436 days.

(21) Appl. No.: 12/356,478

(22) Filed: Jan. 20, 2009

(65) Prior Publication Data

US 2010/0185207 A1 Jul. 22, 2010

(51) Int. Cl.
 *B23P 11/00* (2006.01)
 *B23Q 1/00* (2006.01)
 *B21D 41/00* (2006.01)
 *B21J 7/16* (2006.01)

(52) U.S. Cl. ............... 29/243.5; 29/283; 72/402

(58) Field of Classification Search .......... 269/289 MR, 269/71, 45; 29/281, 559, 243, 526, 243.5, 29/238, 283; 72/402
See application file for complete search history.

(56) References Cited

U.S. PATENT DOCUMENTS

| | | | |
|---|---|---|---|
| 5,947,993 A | 9/1999 | Morales | |
| 5,972,016 A | 10/1999 | Morales | |
| 6,009,614 A | 1/2000 | Morales | |
| 6,051,002 A | 4/2000 | Morales | |
| 6,063,102 A | 5/2000 | Morales | |
| 6,082,990 A | 7/2000 | Jackson et al. | |
| 6,092,273 A | 7/2000 | Villareal | |
| 6,125,523 A | 10/2000 | Brown et al. | |
| 6,141,855 A | 11/2000 | Morales | |
| 6,202,272 B1 | 3/2001 | Jackson | |
| 6,277,110 B1 | 8/2001 | Morales | |
| 6,352,547 B1 | 3/2002 | Brown et al. | |
| 6,387,117 B1 | 5/2002 | Arnold, Jr. et al. | |
| 6,481,262 B2 | 11/2002 | Ching et al. | |
| 6,726,713 B2 | 4/2004 | Schaldach et al. | |
| 6,915,560 B2 | 7/2005 | Austin | |
| 6,920,674 B2 * | 7/2005 | Thornton | 29/270 |
| 7,308,748 B2 * | 12/2007 | Kokish | 29/516 |
| 2005/0240256 A1 * | 10/2005 | Austin | 623/1.11 |

* cited by examiner

*Primary Examiner* — Monica Carter
*Assistant Examiner* — Seahee Yoon
(74) *Attorney, Agent, or Firm* — Fulwider Patton LLP

(57) ABSTRACT

A system for crimping a prosthesis is disclosed, comprising a plurality of wheels. Each wheel has an outer circumferential surface configured to be placed in contact with the prosthesis. When in contact with the prosthesis, each wheel is configured to be rotated, thereby to apply a radially inward force on the prosthesis so as to reduce the diameter of the prosthesis. More than one set of wheels may be provided, so that the prosthesis is crimped first by one set of wheels, then by a subsequent set of wheels.

4 Claims, 7 Drawing Sheets

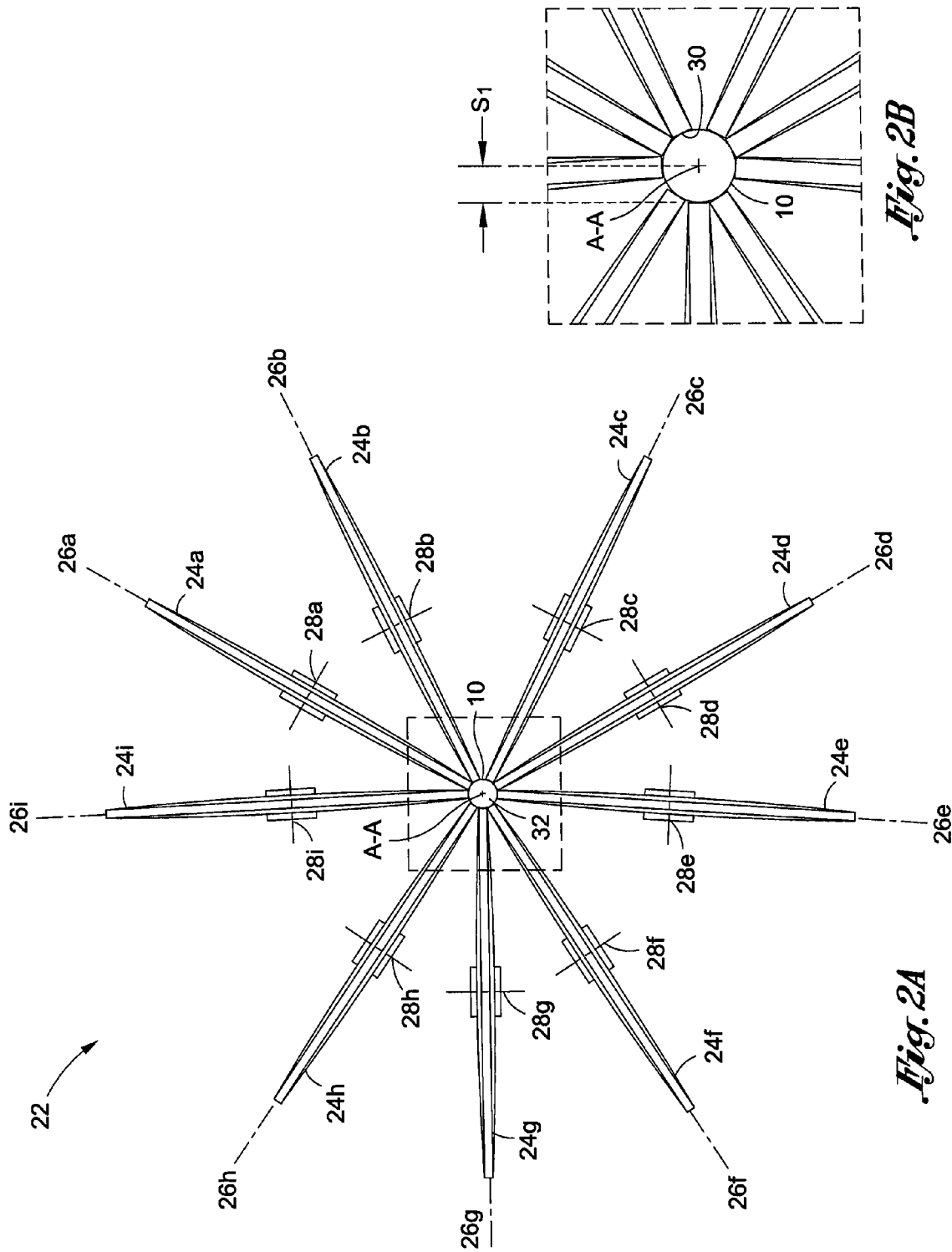

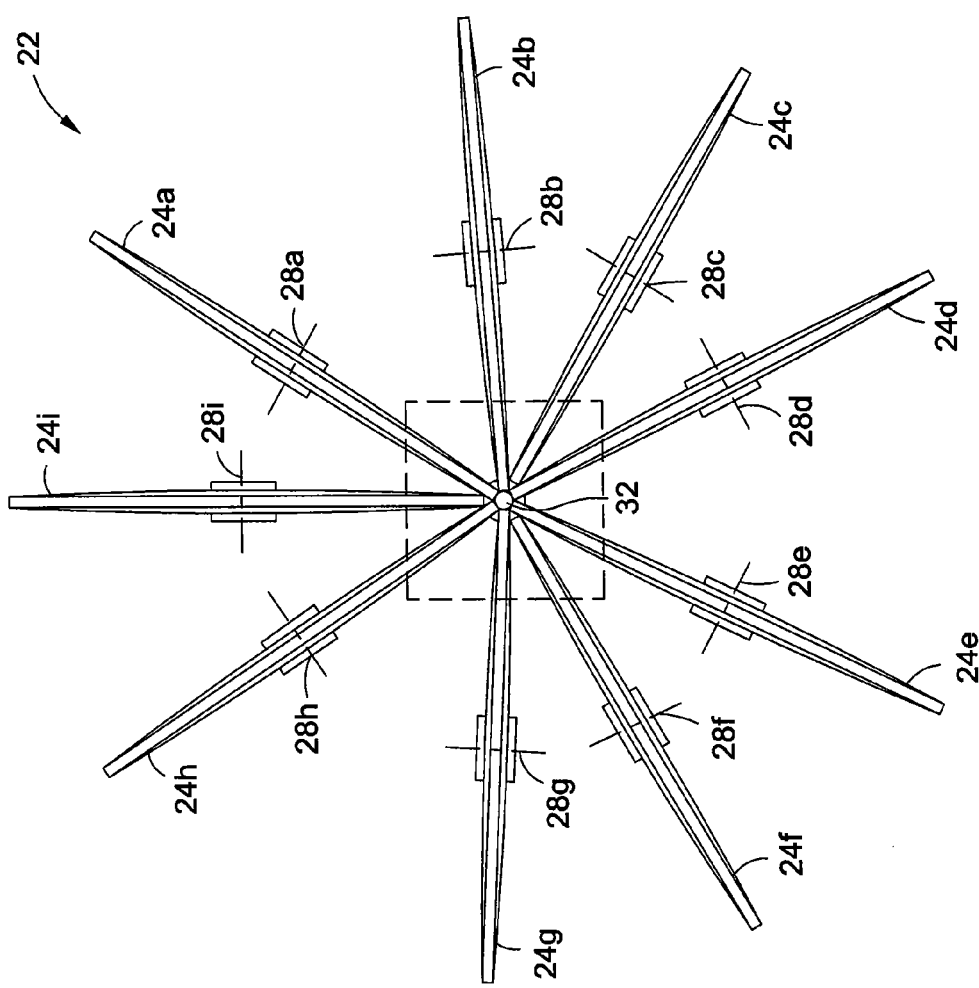
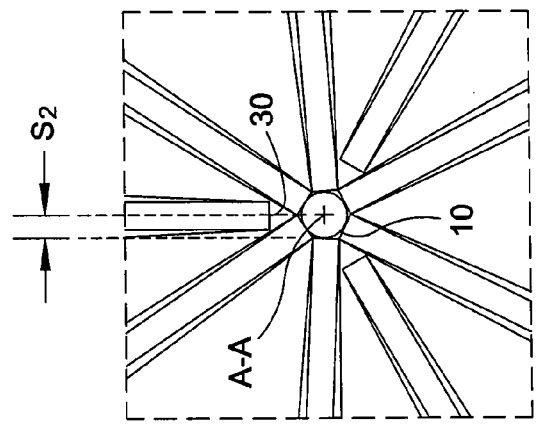
Fig. 3A
Fig. 3B

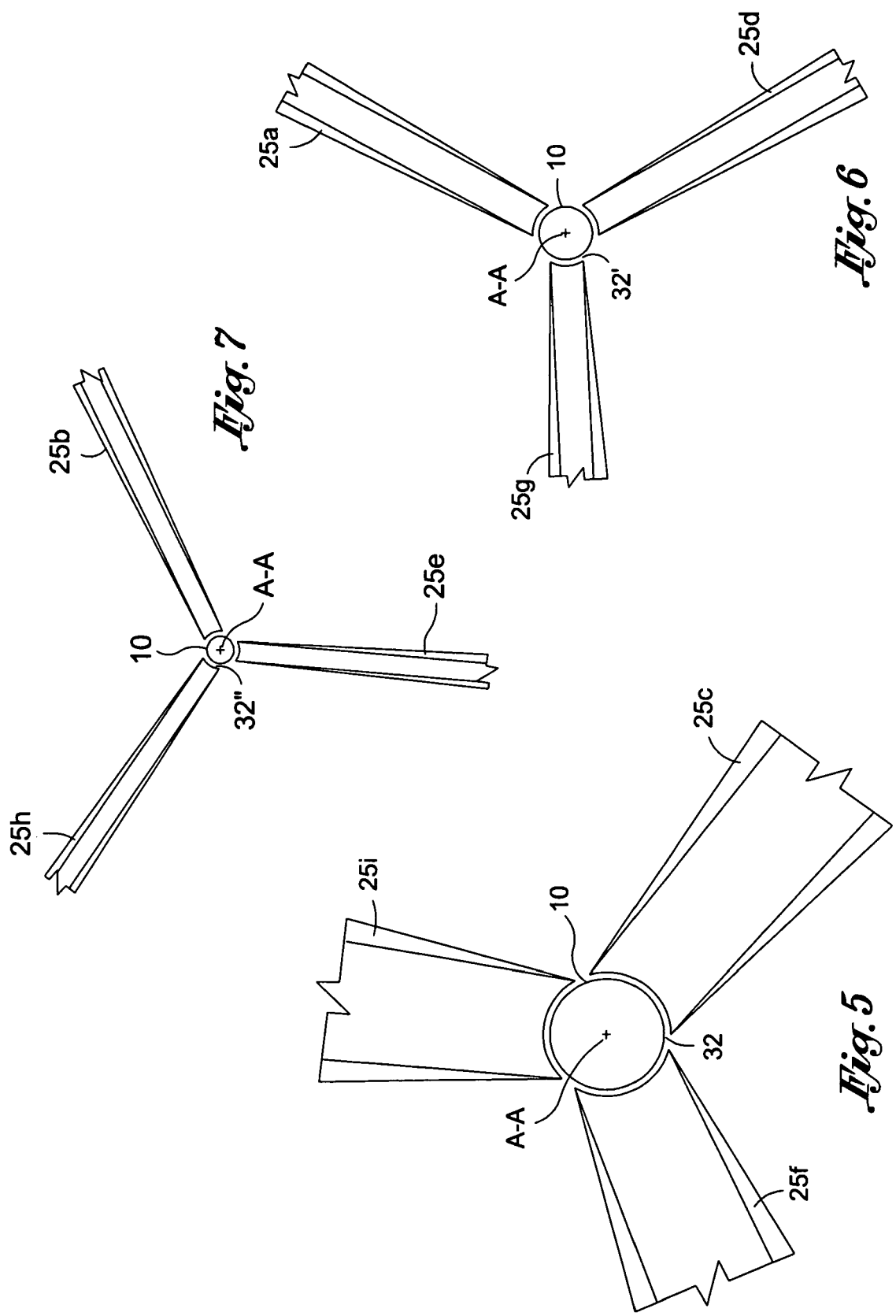

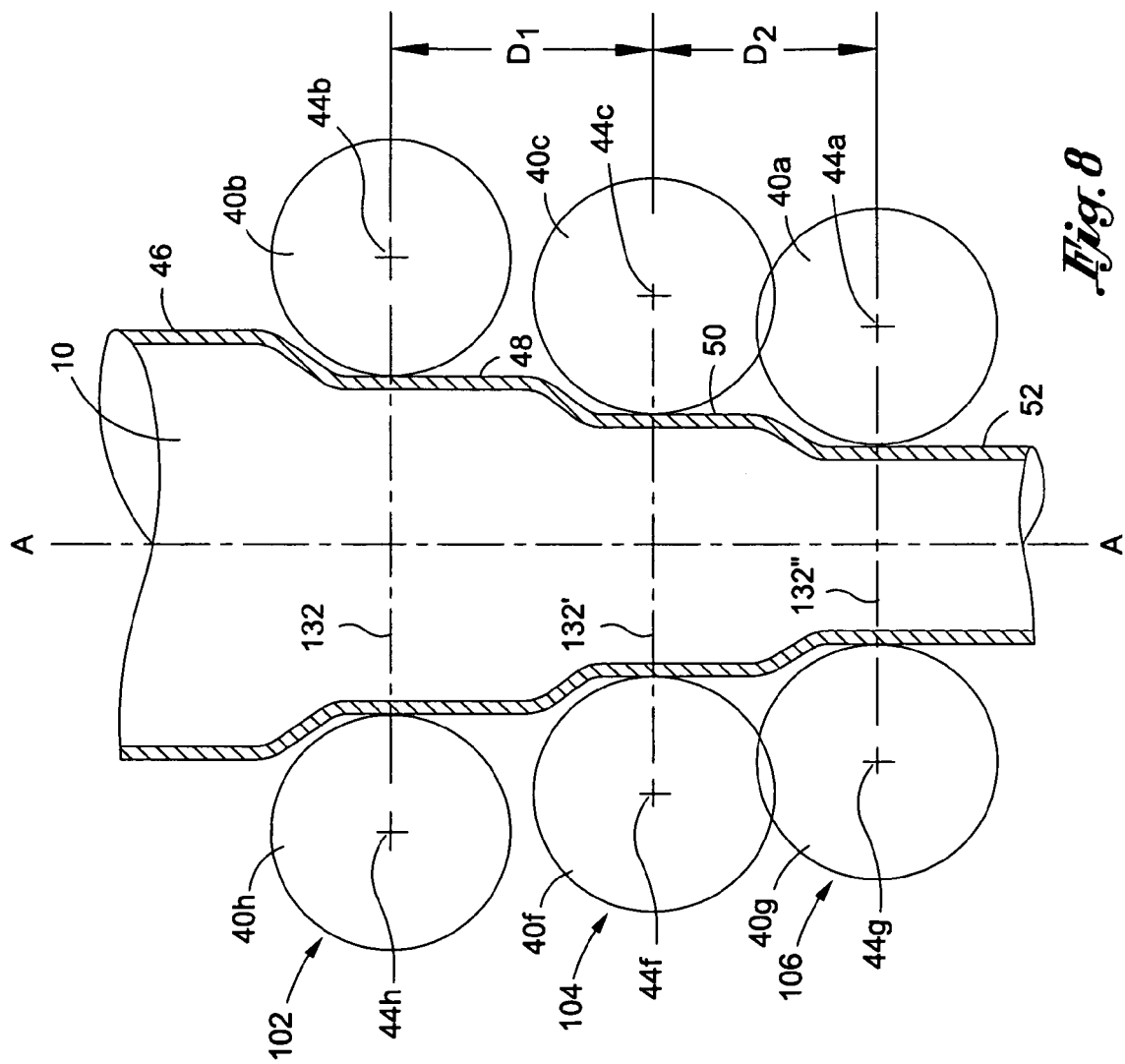

STENT CRIMPING DEVICE

BACKGROUND OF THE INVENTION

The present invention relates to an apparatus for loading a tubular graft or prosthesis, such as a stent, onto the distal end of a catheter assembly of the kind used, for example, in percutaneous transluminal coronary angioplasty (PTCA) or percutaneous transluminal angioplasty (PTA) procedures.

In typical PTCA procedures, a guiding catheter is percutaneously introduced into the cardiovascular system of a patient through the brachial or femoral arteries and advanced through the vasculature until the distal end of the guiding catheter is in the ostium. A guide wire and a dilatation catheter having a balloon on the distal end are introduced through the guiding catheter with the guide wire sliding within the dilatation catheter. The guide wire is first advanced out of the guiding catheter into the patient's coronary vasculature and the dilatation catheter is advanced over the previously advanced guide wire until the dilatation balloon is properly positioned across the arterial lesion. Once in position across the lesion, a flexible and expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

In angioplasty procedures of the kind referenced above, restenosis of the artery may develop over time, which may require another angioplasty procedure, a surgical bypass operation, or some other method of repairing or strengthening the area. To reduce the likelihood of the development of restenosis and to strengthen the area, a physician can implant an intravascular prosthesis for maintaining vascular patency, commonly known as a stent, inside the artery at the lesion. The stent is crimped tightly onto the balloon portion of the catheter and transported in its delivery diameter through the patient's vasculature. At the deployment site, the stent is expanded to a larger diameter, often by inflating the balloon portion of the catheter. The stent also may be of the self-expanding type.

Since the catheter and stent travel through the patient's vasculature, and probably through the coronary arteries, the stent must have a small delivery diameter and must be firmly attached to the catheter until the physician is ready to implant it. Thus, the stent must be loaded onto the catheter so that it does not interfere with delivery, and it must not come off the catheter until it is implanted.

In procedures where the stent is placed over the balloon portion of the catheter, it is necessary to crimp the stent onto the balloon portion to reduce its diameter and to prevent it from sliding off the catheter when the catheter is advanced through the patient's vasculature. Non-uniform crimping can result in sharp edges being formed along the now uneven surface of the crimped stent. Furthermore, non-uniform stent crimping may not achieve the desired minimal profile for the stent and catheter assembly. Where the stent is not reliably crimped onto the catheter, the stent may slide off the catheter and into the patient's vasculature prematurely as a loose foreign body, possibly causing obstructed arteries, blood clots in the vasculature, including thrombosis. Therefore, it is important to ensure the proper crimping of a stent onto a catheter in a uniform and reliable manner.

This crimping is often done by hand, which can be unsatisfactory due to the uneven application of force resulting in non-uniform crimps or loosely fitted stents which pose a critical danger to the patient. In addition, it is difficult to visually judge when a uniform and reliable crimp has been applied.

Some self-expanding stents are difficult to load by hand onto a delivery device such as a catheter. Furthermore, the more the stent is handled the higher the likelihood of human error, which would be antithetical to a properly crimped stent. Accordingly, there is a need in the art for a device for reliably crimping a stent onto a catheter.

There have been attempts at devising a tool for crimping a stent onto a balloon delivery catheter. An example of such a tool comprises a series of plates having substantially flat and parallel surfaces that move in a rectilinear fashion with respect to each other. A stent carrying catheter is disposed between these surfaces, which surfaces crimp the stent onto the outside of the catheter by their relative motion and applied pressure. The plates have multiple degrees of freedom and may have force-indicating transducers to measure and indicate the force applied to the catheter during crimping of the stent.

Another stent loading tool design is comprised of a tubular member housing a bladder. The tubular member and bladder are constructed to hold a stent that is to be crimped onto a balloon catheter assembly. Upon placement of the stent over the balloon portion of the catheter, a valve in the loading tool is activated to inflate the bladder. The bladder compresses the stent radially inward to a reduced diameter onto the balloon portion of the catheter to achieve a snug fit. In this way, the stent is crimped onto the distal end of a balloon catheter with a minimum of human handling. The foregoing stent crimping tools are disclosed in, for example, U.S. Pat. Nos. 5,437,083 and 5,546,646 to Williams et al.

Still another conventional stent crimping tool is manufactured by JOHNSON & JOHNSON and appears similar to a hinged nutcracker. Specifically, the tool is comprised of two hand operated levers hinged at one end and gripped in the palm of the hand at the opposite end. A cylindrical opening holding a crimping tube is provided through the mid-portion of the tool to receive therein a stent loaded onto a balloon catheter. The crimping operation is performed by the user squeezing the handle thereby pressing the crimping tube which in turn pinches the stent onto the balloon catheter.

While the prior art devices are suitable for crimping stents onto balloon catheters, they suffer from problems such as non-uniform crimping forces, especially for long stents, resulting in non-uniform crimps. The present invention addresses these and other needs.

SUMMARY OF THE INVENTION

Both PTCA and PTA procedures have become commonplace in treating stenoses or lesions in blood vessels and coronary arteries. In approximately 35% to 40% of the procedures, restenosis may develop requiring a further angioplasty, atherectomy or bypass procedure to return the patency of the vessel. Intravascular stents are now being deployed after PTCA and PTA procedures, and after atherectomies, in order to help prevent the development of restenosis. Importantly, such stents, mounted on the balloon portion of a catheter, must be tightly crimped to provide a low profile delivery diameter, and to ensure that the stent stays on the balloon until the balloon is expanded and the stent is implanted in the vessel. The present invention is directed to a crimping tool that can repeatedly provide a uniform and tight crimp to ensure the low profile diameter of the stent on the balloon portion of the catheter, and to ensure that the stent remains firmly attached until it is implanted in the vessel by expanding the balloon.

More precisely, the present invention is directed to a tool for crimping a prosthesis onto a catheter comprising a plurality of wheels, wherein each wheel is rotatably mounted on an axle. Each wheel has an outer circumferential surface configured to apply a radially inward force on the prosthesis. The wheels are mounted so as to be positionable in relation to each other such that a diameter of each wheel radiates outwardly from a central axis, wherein the outer circumferential surfaces of the wheels are positionable equidistant from the axis by a first smallest possible distance ("S1" as in FIG. 2B) to define a first space that includes the axis. This configuration permits a prosthesis to be passed between the wheels which apply a radially inward force on the prosthesis to crimp the prosthesis to a smaller diameter. A first number out of the plurality of wheels are mounted so as to be restrained from further advancing toward the axis, thereby leaving a number of remaining wheels mounted to be capable of further advancing toward the axis, wherein the outer circumferential surfaces of the remaining wheels are positionable equidistant from the axis by a second smallest possible distance ("S2" as in FIG. 3B) to define a second space that includes the axis, the second space being smaller than the first space. In this way, the remaining wheels are advantageously positioned to further crimp the prosthesis to an even smaller diameter, which would otherwise be impossible if the first number of wheels were not configured to be restrained from further advancing toward the axis.

In another aspect, the invention includes a method of crimping a prosthesis having an elongate axis. The method comprises positioning a plurality of wheels about the prosthesis so that an outer circumferential surface of each wheel is in contact with the prosthesis; moving the prosthesis along the elongate axis; rotating each of the wheels while maintaining contact between the wheels and the prosthesis, thereby reducing the diameter of the prosthesis; causing a first number of the wheels to no longer be in contact with the prosthesis to leave a first remainder of wheels in contact with the prosthesis; and rotating each of the first remainder of wheels while maintaining contact between each of the first remaining wheels and the prosthesis, thereby further reducing the diameter of the prosthesis. This method has a similar advantage to the foregoing apparatus, of sequentially crimping the prosthesis to a final diameter, using a first number of wheels and then subsequently a second smaller number of wheels to finish off the crimping to the desired final diameter.

In yet a further aspect, the invention includes a system for crimping a prosthesis having an elongate axis comprising a first plurality of wheels, wherein each wheel is rotatably mounted on an axle and each wheel has an outer circumferential surface having a first width. The wheels are configured to be positionable in relation to each other such that a diameter of each wheel radiates outwardly from a central axis, whereby the outer circumferential surfaces of the wheels define a first space that includes the central axis, the first space being configured to receive the prosthesis during crimping. A second plurality of wheels is provided, wherein each wheel is rotatably mounted on an axle and each wheel has an outer circumferential surface having a second width. The second plurality of wheels are configured to be positionable in relation to each other such that a diameter of each wheel radiates outwardly from the central axis, whereby the outer circumferential surfaces of the second plurality of wheels define a second space that includes the central axis, the second space being configured to receive the prosthesis during crimping. Significantly, in this embodiment, the first width is greater than the second width, thereby allowing the second plurality of wheels to take the prosthesis down to a smaller diameter than the first plurality of wheels can reasonably achieve.

And in yet a further aspect, the invention includes a method of crimping a prosthesis having an elongate axis. The method comprises positioning a first plurality of wheels about the prosthesis so that an outer circumferential surface of each wheel is in contact with the prosthesis, each surface having a first width; moving the prosthesis along the elongate axis; rotating each of the wheels while maintaining contact between the wheels and the prosthesis, thereby reducing the diameter of the prosthesis. Then, removing all of the first plurality of wheels from being in contact with the prosthesis; positioning a second plurality of wheels about the prosthesis so that an outer circumferential surface of each of the second plurality is in contact with the prosthesis, each surface having a second width less than the first width; moving the prosthesis along the elongate axis; rotating each of the second plurality of wheels while maintaining contact between the second plurality of wheels and the prosthesis, thereby further reducing the diameter of the prosthesis.

An even further aspect of the invention includes a system for crimping a prosthesis comprising a first plurality of wheels, wherein each wheel is rotatably mounted on an axle, and each axle of the first plurality lies in the same first plane. Each wheel has an outer circumferential surface and the wheels are positioned in relation to each other such that a diameter of each wheel radiates outwardly from a central axis, whereby the outer circumferential surfaces of the wheels define a first space that includes the central axis, the first space being configured to receive the prosthesis during crimping. A second plurality of wheels is provided wherein each wheel is rotatably mounted on an axle, and each axle of the second plurality lies in the same second plane, the second plane being spaced apart from the first plane by a distance. Each wheel has an outer circumferential surface and the wheels are positioned in relation to each other such that a diameter of each wheel radiates outwardly from the central axis, whereby the outer circumferential surfaces of the wheels define a second space that includes the central axis, the second space being configured to receive the prosthesis during crimping. Significantly, the first space is larger than the second space. By this structure, a prosthesis may advantageously be crimped when the prosthesis is unusually long. The spaced apart sets of wheels allow for greater control over the crimping process as the prosthesis passes from one set to the next.

Finally, the invention includes a method of crimping a prosthesis having an elongate axis comprising moving the prosthesis along its axis between a first plurality of wheels so that an outer circumferential surface of each of the first plurality of wheels is in contact with the prosthesis; rotating each of the wheels while maintaining contact between the wheels and the prosthesis, thereby reducing the diameter of the prosthesis by a first amount; passing the prosthesis from between the first plurality of wheels to between a second plurality of wheels, the second plurality of wheels being situated adjacent the first plurality; moving the prosthesis between the second plurality of wheels so that an outer circumferential surface of each of the second plurality of wheels is in contact with the prosthesis; rotating each of the second plurality of wheels while maintaining contact between the wheels and the prosthesis, thereby further reducing the diameter of the prosthesis by a second amount. In this embodiment, the invention has advantages similar to those of the previously described embodiment, in which a long prosthesis may be crimped under improved control of one set of wheels adjacent a second set of wheels.

The present invention is thus capable of homogeneously and precisely crimping a stent onto a balloon catheter. Such a crimping tool is highly useful to cardiologists and radiologists, for example. Such physicians are constantly concerned with proper deployment of the stent within the patient that it is desirable to have a consistently and reliably crimped stent. The present invention tool is further a time saver, because the stent crimping procedure can be performed fairly efficiently and quickly. Indeed, these and other advantages of the present invention will become apparent from the following detailed description thereof when taken in conjunction with the accompanying exemplary drawings.

BRIEF DESCRIPTION OF THE DRAWINGS

FIG. 2a shows a schematic top plan view of a first embodiment of the present invention stent crimping system employing nine radially distributed wheels, with the wheels set in a first position.

FIG. 2b shows a detail from FIG. 2a, as indicated.

FIG. 3a shows a schematic top plan view of the embodiment of FIGS. 2a and b, with the wheels set in a second position.

FIG. 3b shows a detail from FIG. 3a, as indicated.

FIG. 5 shows a partial top plan view of the embodiment of FIG. 4, showing the wheels set in a second position.

FIG. 6 shows a partial top plan view of the embodiment of FIG. 4, showing the wheels set in a third position.

FIG. 7 shows a partial top plan view of the embodiment of FIG. 4, showing the wheels set in a fourth position.

FIG. 8 shows a schematic partial side view of a third embodiment of the invention, showing features of the invention.

DETAILED DESCRIPTION OF THE PREFERRED EMBODIMENTS

With reference to FIGS. 2-9, there is shown by way of exemplification and not limitation a prosthesis or stent crimping device having features of the present invention, generally indicated by the numeral 22.

Figure 1:
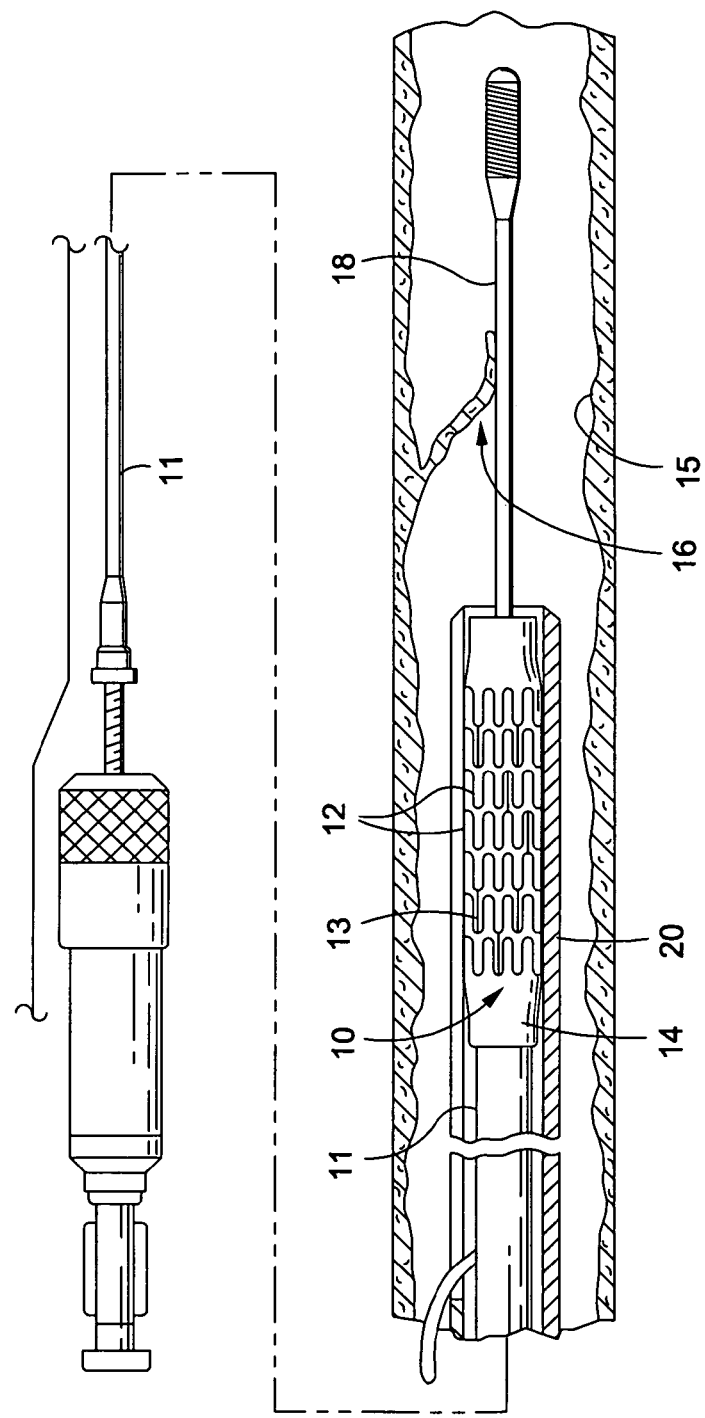
FIG. 1 shows a schematic side elevational view, partially in section, depicting a stent that has been crimped onto a delivery catheter and disposed within a vessel.

Before the invention is described, several aspects of related technology and human anatomy are described with reference to FIG. 1, which illustrates an intravascular stent 10 which is mounted onto a delivery catheter 11. The stent 10 generally comprises a plurality of radially expandable cylindrical elements 12 disposed generally coaxially and interconnected by members 13 disposed between adjacent cylindrical elements 12. Delivery catheter 11 has an expandable portion or balloon 14 for expanding stent 10 within coronary artery 15 or other vessel such as saphenous veins, carotid arteries, arteries, and veins. Artery 15, as shown in FIG. 1, has a dissected lining 16 which has occluded a portion of the arterial passageway.

The delivery catheter 11 onto which the stent 10 is mounted is essentially the same as a conventional balloon dilatation catheter for angioplasty procedures. The balloon 14 may be formed of suitable materials such as polyethylene, polyvinyl chloride, polyethylene terephthalate, nylon and other like polymers. In order for the stent 10 to remain in place on balloon 14 during delivery to the site of the damage within artery 15, the stent 10 is compressed onto balloon 14. This compressing step is known as crimping.

An optional retractable protective delivery sleeve 20 may be provided to further ensure that stent 10 stays in place on balloon 14 of delivery catheter 11 and to prevent abrasion of the body lumen by the open surface of stent 10 during delivery to the desired arterial location. Other means for securing stent 10 onto balloon 14 may also be used, such as providing collars or ridges on the ends of the working portion, i.e., the cylindrical portion of balloon 14.

In order to implant stent 10, it is first mounted onto inflation balloon 14 on the distal extremity of delivery catheter 11. Stent 10 is crimped down onto balloon 14 to ensure a low profile. The present invention addresses this crimping procedure by describing a system and method for the same.

The catheter-stent assembly can be introduced into the patient's vasculature through processes known in the art. Briefly, guide wire 18 is disposed across the arterial section where an angioplasty or atherectomy has been performed requiring a follow-up stenting procedure. In some cases, the arterial wall lining may be detached so that guide wire 18 is advanced past detached or dissected lining 16 and the catheter-stent assembly is advanced over guide wire 18 within artery 15 until stent 10 is directly under detached lining 16. Prior to inflation of balloon 14, delivery sleeve 20 is retracted to expose stent 10. Depending on the balloon and stent assembly, a delivery sleeve may be unnecessary. Balloon 14 of delivery catheter 11 is then inflated using an inflation fluid. Expansion of balloon 14 in turn expands stent 10 against artery 15. Next, balloon 14 is deflated and catheter 11 is withdrawn leaving stent 10 to support the damaged arterial section. As mentioned above, in order to ensure proper seating of stent 10 on balloon 14, and to ensure proper deployment of stent 10 at the site of the damage within artery 15, the stent crimping procedure is important.

FIGS. 2a and 2b show a schematic top plan view, and detail, of a system or device exemplifying a preferred embodiment of the present invention stent crimping tool 22. As recognized in this top plan view, the present invention stent crimping tool 22 is characterized by a plurality of wheels 24a, 24b, 24c, 24d, 24e, 24f, 24g, 24h, 24i, arranged about a central axis A-A (extending perpendicularly into the page, as seen in FIG. 2). Preferably, the wheels are arranged evenly about the axis A-A. Each wheel defines its own central plane 26a, . . . 26i. The wheels are arranged so that the plane of each wheel passes through the central axis A-A, and extends radially outwardly from the central axis. Each wheel is configured to rotate about its own axle 28a, . . . 28i. All of the axles lie in a common plane through which the axis A-A perpendicularly passes. Each wheel has an outer circumferential surface 30, best seen in FIG. 2b. These surfaces face toward the axis A-A, and define a space 32 between them. While nine wheels are shown in this embodiment, other numbers of wheels are contemplated to be within the scope of the invention.

Once the wheels are assembled as described and shown, a stent to be crimped is positioned in relation to the wheels. Such stent 10 is positioned coaxial with the axis A-A. The stent is positioned upon a catheter (not shown in FIGS. 2-9) onto which the stent is to be crimped. The catheter may take any of the forms described herein, including balloon catheter, non-balloon catheter etc. The manner in which the stent is crimped using the system of the present invention may take place under a number of preferred embodiments. In each embodiment, the general principle is applied that the outer surface 30 of each of a plurality of wheels is positioned against the stent, which is held with its own axis co-axial with the axis A-A. At least one wheel may be driven to rotate. The other wheels may either be driven, or as will be appreciated, they may rotate in unison with the driven wheel due to their contact with the stent that is forced to move axially in response to the rotated wheel. The rotation of the wheels, and the friction between the surfaces 30 and the stent, causes the stent to move axially along axis A-A. Thus, each wheel applies a radially inward force on the stent. The magnitude of this inward force will depend on the size of the space 32 that has been selected to be formed between the surfaces 30 of the wheels 24a, etc., in relation to the size of the stent 10. These forces gradually move axially along the length of the stent as the stent passes between the wheels along axis A-A. It will be appreciated that the plurality of wheels effectively surround the stent, so that the stent experiences a circumferentially inward force that gradually moves along the length of the stent axis. This application of circumferentially inward forces along the axis of the stent has the effect of uniformly crimping the stent radially inwardly onto the catheter, after which catheter and stent 10 are removed for further treatment and/or processing in which an outer sheath such as sheath 20 (FIG. 1) may be fitted over the outside of the stent, and the like.

Turning now to aspects of different preferred embodiments under which the above described general application of radially inward forces may be applied to the stent. Referring to FIG. 2, there is first seen how an uncrimped stent 10, with an original uncrimped diameter, is positioned between nine wheels 24a-24i arranged equidistantly about the axis A-A of the stent. The external circumferential surface 30 of each wheel is positioned adjacent the stent to form a space 32 between the wheels that, in use, includes the stent. Preferably, the stent is positioned on a catheter that is supported by a mandrel or guidewire (not shown) to support the catheter and balloon as the stent is crimped. By supporting and moving the mandrel, the stent itself may be supported and moved in relation to the wheels. To commence the crimping process, one or more wheels are rotated under power, and the stent is fed (by manipulating the mandrel) into the space 32 between the wheels. It should be appreciated that the size of the space 32 will be judiciously selected to approximate the diameter of the stent that is desired after a first pass between the wheels. Although, it should be appreciated, it is necessary for only one wheel to be driven or rotated under power, in a preferred embodiment all the wheels are rotated under power to provide a uniformly crimped stent configuration. Rotation of the wheels is configured in relation to the mandrel to be accompanied by relative axial movement of the stent at the same velocity as the tangential velocity of the wheels at their points of contact with the stent. This aspect allows the stent to receive a radially inward force applied by each wheel without any shear force being exerted at the surface of the stent. Where only one wheel is driven, this driven rotation will, due to the contact by all of the wheels with the stent, cause the other wheels also to rotate as the stent moves past the remaining undriven wheels.

It should be appreciated that by merely passing the stent once through the space 32 between the wheels while they are under rotation will not necessarily impart a crimped diameter of desired magnitude to the stent. This is firstly because a certain amount of elastic recovery may be achieved by the stent once it has passed between the wheels, and secondly because it may be undesirable to impart the final desired crimped diameter in one pass. Thus, a second pass in the other direction, and even a third pass, may be desired to bring the stent to a desired uniform diameter, while the space between the wheels is held under a constant geometry or slightly reducing geometry. Once the stent has achieved a desired diameter, the space 32 between the wheels may be reduced in size by moving the wheels in unison closer toward the axis A-A so that they remain equidistant from the axis. Yet again, the diameter of the stent may be reduced by a series of passes through the space 32 while the wheels are driven to apply a radially inward force on the stent (the force effectively extending around the circumference of the stent), while the force moves axially up and down the exterior of the stent in the absence of any surface shear force.

It will be further appreciated that there is a limiting factor in how small the space 32 may be reduced by advancing the wheels toward the axis A-A is the width of the wheels, because there may come a point where the space 32 cannot be made any smaller by advancing the wheels toward the axis A-A in that the wheels may tend to butt up against each other and prevent further reduction of the space 32. Desirably, on the one hand, the width of the wheels should not be too narrow because a wheel may apply too narrow a load on the stent, capable of bending the stent locally rather than crimping it. On the other hand, a broader set of wheels results in a large minimum space 32 which may be larger than desired. Thus, in yet another aspect of the invention, exemplified in FIG. 3, the wheels are mounted on their axles to permit some of the wheels 24b, 24c, 24e, 24f, 24h, 24i so that they cease advancing in unison towards the axis A-A, or they even be moved away from the axis A-A. By ceasing the advance of, or removing, some of the wheels, the remaining wheels 24a, 24d, 24g can be moved even closer toward the axis A-A unhindered. Thus, as exemplified in FIG. 3, in a preferred embodiment, three of the nine wheels may initially be held stationary with respect to the axis A-A, or be moved away from the axis A-A, leaving six wheels to form the much reduced space 32 through which the stent must pass for crimping under the radially inward force of the remaining wheels. Subsequently, another three wheels may be held back or retracted, leaving only three wheels to form an even more reduced space 32 through which the stent must pass for crimping. Therefore, by configuring the mounting of each wheel to selectively permit some wheels to be held back from the axis A-A or retracted, a system is provided that advantageously allows the remaining wheels to finish off the crimping process when the stent has reached its smallest diameter.

Figure 4:
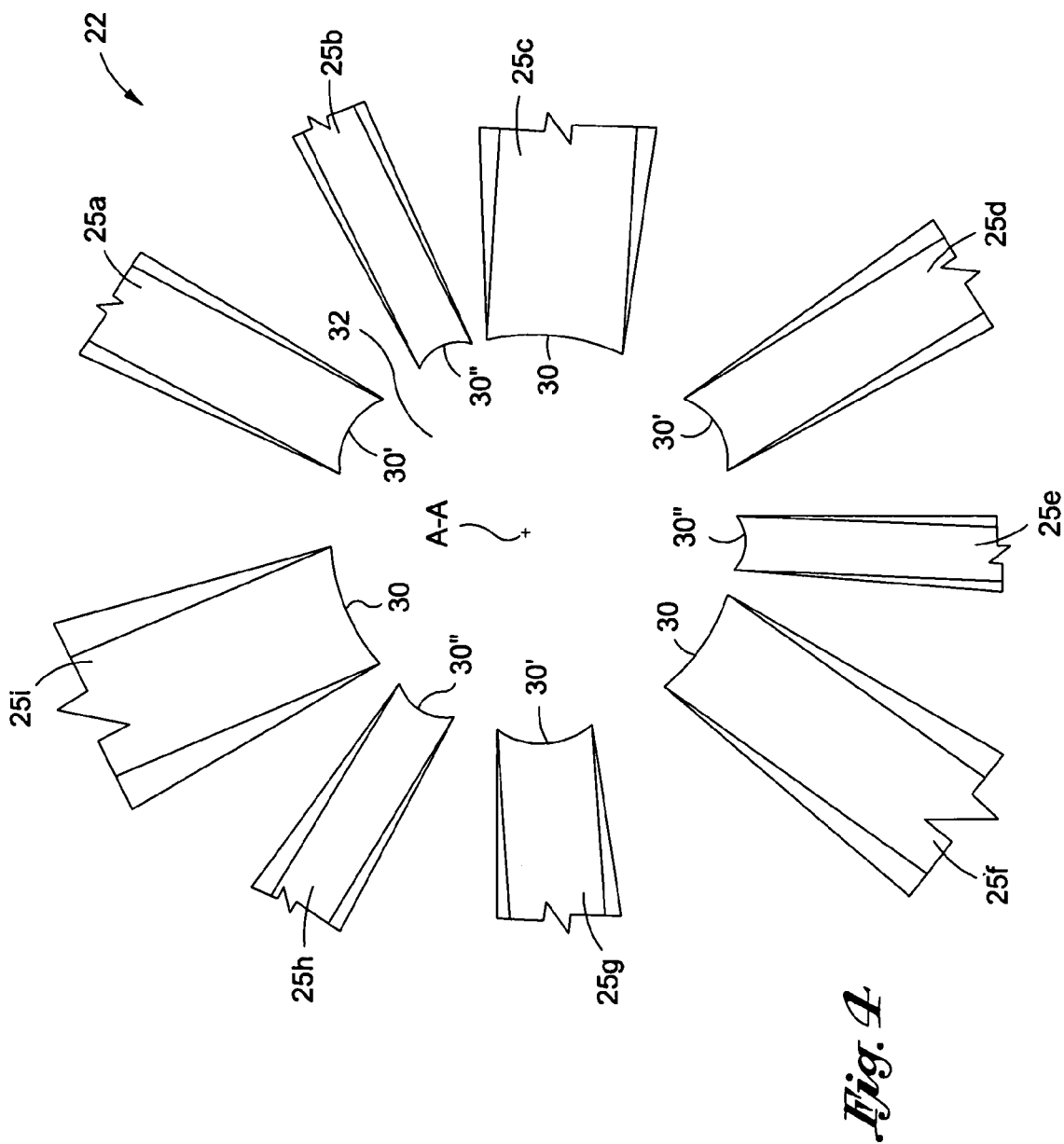
FIG. 4 shows a schematic partial top plan view of a second embodiment of the present invention, showing features of the invention, with wheels set in a first position.

Turning now to another aspect of the invention, there is shown with reference to FIGS. 4-7 how a plurality of wheels may be configured to provide a graduated crimping effect using a different embodiment than the one described above. In this embodiment, nine wheels 25a-25i (as seen in FIG. 4) each may have the same diameter as in the previous embodiment, but different sets of wheels may have different widths, in decreasing magnitude. Thus, for example, of the nine wheels, in a first set of three wheels 25i, 25c, 25f (as seen in FIG. 5) each wheel has a circumferential surface 30 with a broadest width, in a second set of three wheels 25a, 25d, 25g (as seen in FIG. 6) each wheel has a circumferential surface 30' with a narrower width, and in a third set of three wheels 25b, 25e, 25h (as seen in FIG. 7) each wheel has a circumferential surface 30" with a narrowest width.

This second embodiment operates differently than the first embodiment in that only one set of three wheels is deployed in a crimping action at any one time. The broadest set is used first as exemplified in FIG. 5, when the stent 10 is in its largest uncrimped diameter. Preferably, the outer circumferential surface 30 of each wheel may be given a slight curvature along its width, to conform with the diameter of the stent. It will be appreciated that the diameter of the stent will move from a first diameter to a second smaller diameter as it undergoes crimping with the first set of wheels, so the curvature of the surface on the outer wheel circumference may preferably be chosen to conform with the midpoint diameter of the stent, lying half way between the first and the second diameters. Thus, in operation, the first set of three wheels are brought together to provide a first space 32 between them (FIG. 5). The stent is then passed into the space and the wheels are set in motion. As before, a radially inward force is applied to the stent by the wheels, but in this embodiment, there are only three wheels applying the force initially, each force occupying a broader extent of the stent circumference. Preferably, the width of the wheels is set to provide a substantially uniform force around the circumference of the stent. As before, the stent may be manipulated via a mandrel extending through the catheter, and the stent may be passed back and forth through the space while the wheels turn.

Once the first set of wheels have imparted a desired crimped diameter to the stent, the first set of wheels 24*i*, 24*c*, 24*f* (FIG. 5) may be withdrawn, and the second set 24*a*, 24*d*, 24*g* (FIG. 6), having a narrower width, are moved up toward the axis A-A to provide a second space 32' between them. It will be appreciated that a narrower set of wheels is capable of forming a second space that is smaller than the first space 32. In the same way, a slight curvature may be imparted to the outer circumferential surface 30' of the second set of wheels along its width, the curvature being chosen to conform with a diameter of the stent between the range of diameters it will assume while undergoing crimping. As with the first set of wheels, the second set of wheels is used to further crimp the stent down to a smaller overall diameter.

Finally, if the crimping thus done is not sufficient, the second set of wheels may be withdrawn, and the third set of wheels 24*b*, 24*e*, 24*h* (FIG. 7), having a yet narrower width than the second set, are moved up toward the axis A-A to provide a third space 32" between them that is smaller than the second space 32'. Likewise, a curvature may be imparted to the outer circumferential surface 30" of the third set of wheels along their width. By following the same procedure as before, a final desired crimped diameter may be imparted to the stent with minimal trauma to the underlying catheter and/or balloon. Of course, further wheel sets may be added to the third set, as required.

Turning now to a third embodiment of the invention, a final aspect of the invention is described with reference to FIGS. 8-9. In this embodiment, principles similar to those of the previous embodiments are employed. However, instead of moving sets of wheels toward and away from the stent after each progressive crimping action, as in the previous embodiment, in this third embodiment, sets of wheels are placed in fixed position, one set stacked vertically under the other and spaced vertically apart from the one above, by a certain distance. Although the wheels are preferably in fixed position during a crimping operation, the wheels may be adjusted both vertically (i.e. one set towards or away from another set) and radially (i.e., towards or away from the axis A-A) as required.

Figure 9:
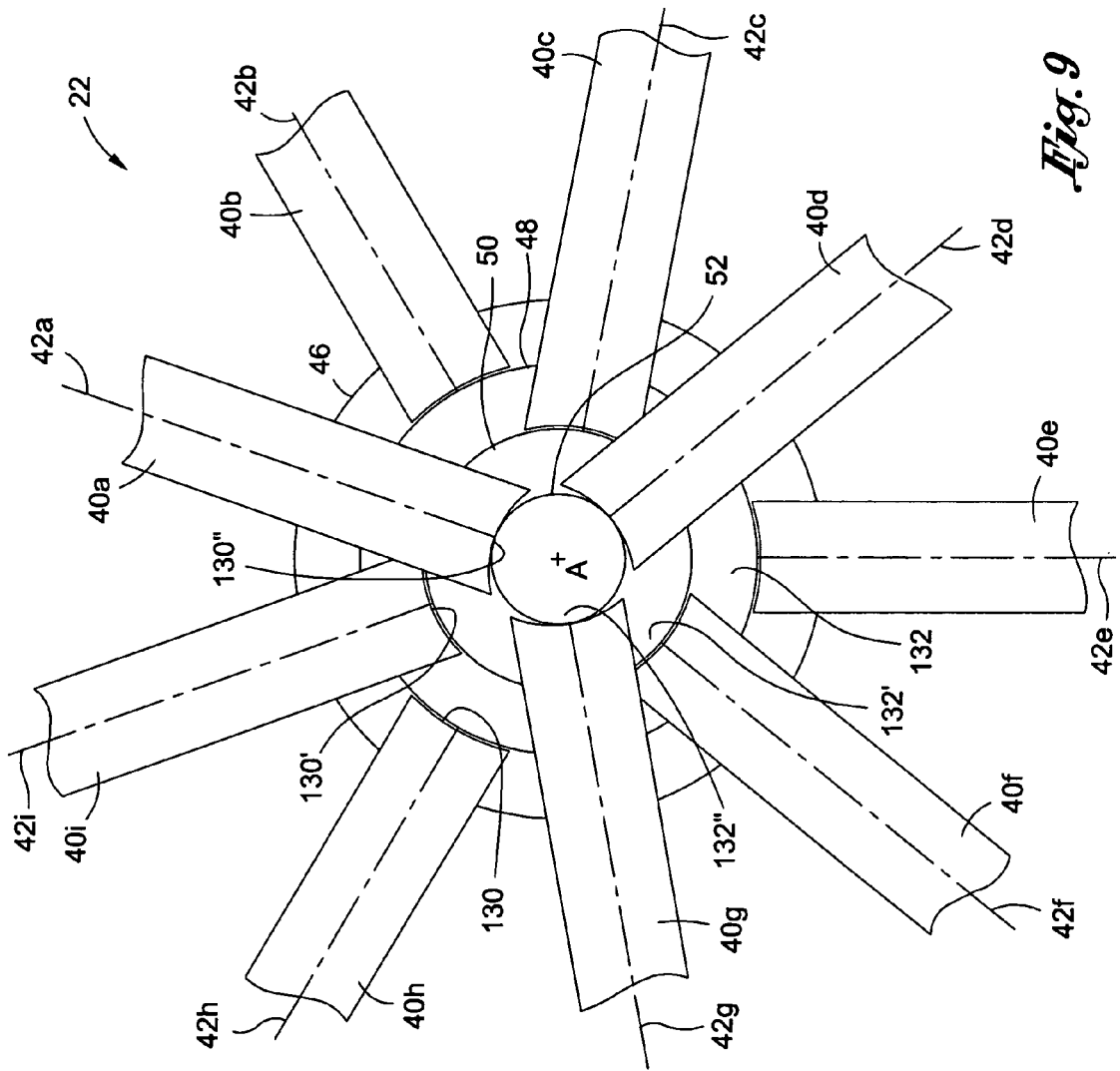
FIG. 9 shows a schematic bottom view of the embodiment of FIG. 8.

As exemplified in FIGS. 8 and 9, a first set 102 of wheels 40*h*, 40*b*, 40*e* (wheel 40*e* is not seen in FIG. 8) is positioned about a central axis A-A, each wheel lying in its own plane 42*h*, 42*b*, 42*e* (FIG. 9) that radiates outwardly from the axis to leave a small space 132 between the wheels. Each wheel turns upon its own axle 44*h*, 44*b*, 44*e* etc. Each axle of the first set of wheels lies in the same first plane. A circumferential surface 130 of each wheel faces toward the axis A-A. As in the previous embodiment, the surface 130 may be curved to accommodate the radius of a stent, and the width of the wheels may be reduced from one set to the next, as explained below. Preferably, but not necessarily, three wheels are included in each set. Other numbers of wheels per set are considered to be within the scope of the invention. In the first set, the wheels are positioned sufficiently far apart from the axis A-A that the space 132 is large enough to receive an unexpanded stent loaded onto a mandrel with guidewire (not shown), and to allow the loaded stent to pass through the space 132 while moving downward along the axis A-A. The size of the space 132 may be adjusted by setting the wheels apart a desired distance, and then fixing the distance during crimping operations. As in the previous embodiment, movement of the stent along the axis A-A may be achieved by manipulating the mandrel (or guidewire) onto which the stent is loaded. The space 132 is sized so that, as the stent is passed through the space 132 between the wheels, the stent is radially compressed from its first uncompressed diameter 46 to a second smaller diameter 48. Such compression may either result in plastic deformation of the elements of the stent so that the stent assumes a permanently reduced diameter, or (in the case of a self expanding stent) it may result in elastic compression of the stent which is impermanent. Further alternatively, such compression may be applied to a stent made of memory alloy such as Nitinol.

With further reference to FIGS. 8 and 9, a second set 104 of wheels 44*i*, 44*c*, 44*f* (wheel 44*i* is not seen in FIG. 8) is positioned below the first set 102, in that each axle of the second set of wheels lies in the same second plane that is spaced below the first plane. The mounting of the wheels on their axles is such that the vertical distance D1 between the first set 102 and the second set 104 of wheels is preferably capable of being adjusted. But once the desired distance between the two wheel sets is achieved for use, that distance is preferably held fixed. The second wheel set, like the first set, comprises a number of wheels (preferably numbering three) all radiating outwardly from the axis A-A. Each wheel has a circumferential surface 130' that faces the axis A-A, and that is curved to accommodate the radius of a stent, and the width of the wheels of the second set may be narrow than that of the first set. The wheel faces 130' define a space 132' that is smaller than the space 132, and may be adjusted to a desired size before crimping operations. In order to permit the second set of wheels to be positioned close to the first set (so that D1 may be a short distance), the wheels of each set are offset from each other by about 40-80 degrees about axis A-A (as seen in FIG. 9) so that, when viewed from the side (as in FIG. 8), the wheels of the one set may vertically overlap with the wheels of the next set, yet not collide with each other.

In similar fashion, a third set 106 of wheels 44*a*, 44*d*, 44*g* (wheel 44*d* is not seen in FIG. 8) is positioned a vertical distance D2 below the second set, in that each axle of the third set of wheels lies in the same third plane that is spaced D2 below the second plane. Again, this vertical distance is capable of being adjusted, and fixed once the desired distance is satisfactory. The third set of wheels adjustably defines a space 132" between them that is smaller than space 132'. Again, the vertical distance D2 may be reduced to a desired amount by off-setting the third set 106 of wheels from both the first set and the second set (as best seen FIG. 9).

Once a plurality of wheel sets are arranged in a spaced apart vertical relationship to each other as described, the device is used as follows. A stent or prosthesis is mounted onto a catheter or mandrel (not shown), that may include a guidewire. Manipulation and movement of the stent is achieved by manipulating the mandrel or catheter upon which the stent is mounted. The catheter (preferably, on a guidewire) is threaded sequentially through the spaces 132, 132' and 132" to extend coaxially with the axis A-A. At least one wheel of each set may then be driven under power, although preferably all wheels may be driven to provide a uniformly crimped stent. The mounted stent is then fed downwardly through the first space 132 where the rotating wheels impart a first crimping effect from radially inward force applied by the wheels, and reduce the diameter of the stent from its original uncrimped diameter 46 to a smaller second diameter 48 that includes some degree of crimping. A short distance after emerging from the space 132 between the first set of wheels, the stent passes through the second space 132' between the second set of wheels, where the stent receives another incremental crimping force by which its diameter is further reduced to a third diameter 50. Then, a short distance after emerging from the second space 132' between the second set 104 of wheels, the prosthesis passes through the third space 132" between the third set 106 of wheels where it receives yet another incremental crimping by which its diameter is yet further reduced to a fourth diameter 52. In a preferred embodiment, three sets of wheels are provided, although more or fewer sets may be provided where needed to achieve the desired degree of crimping.

When the stent finally passes downwardly from the space 132" defined by the last set of wheels 106, it may be passed into a sheath 20 (such as seen in FIG. 1) or containment means configured to hold the stent securely on the catheter. It will be appreciated that in the case of a self expanding stent this is a necessary step to finalizing the crimping process. In the case of a balloon expanded stent, a sheath is often installed to cover the stent during delivery through a body lumen, so that the stent does not injure the walls of the lumen as it passes through the lumen. Passing the crimped stent mounted on a catheter into a sheath may be achieved by known means (not shown), wherein the sheath is slightly heated, then passed over a cylinder that is in turn passed over the stent mounted on catheter. The cylinder may be removed, leaving the sheath to surround the stent. Subsequent retraction of the sheath from the stent allows the stent free to be deployed, whether by self expanding means or by balloon expanding means.

It will be appreciated that the vertical distance separating one set of wheels from the next (e.g. D1, D2) will depend on a number of factors. For example, if the stent or prosthesis is to be plastically deformed by passage between the wheel sets, the vertical distance between wheel sets may be longer than if the stent is self-expanding. Another factor is the required diameter of the stent, both before and after passage between the wheels. Ultimately, the optimal distance of separation between wheel sets may be determined by experimentation, to achieve the desired degree of crimping by each wheel set so that the starting diameter is reduced to the desired final reduced diameter without excessive recoil and the like. A significant advantage of the present invention arising from the vertical separation of crimping wheel sets is that stents that are unusually long are manageable and easy to crimp in a progressive manner. Typically, when long stents are crimped, it is difficult to maintain control of the stent which may tend to elastically expand slightly after initial crimping. When such happens in an uncontrolled environment, the process may become complicated and the even outer surface of the stent may be disrupted.

Further aspects of the invention are now described. While in one embodiment the invention may be used to impart a purely plastic deformation or elastic deformation to the stent during the crimping process, it is also contemplated that the same invention may be used to crimp stents that are composed of "memory" alloys such as Nitinol. When used on such stents, the entire device may be enclosed in a cooling environment (not shown) so that, as the diameter of the stent is reduced by repeated passage between the wheels, the cooling effect will cause the stent to retain its reduced diameter.

Under any of the above embodiments, once the stent has been crimped to a desired diameter, an outer sheath, such as seen in FIG. 1 as sheath 20 may be inserted over the catheter and stent using conventional means. Where the stent has been crimped through plastic deformation, the sheath protects the stent during delivery to a desired location within a patient's vascular system. Removal of the sheath permits inflation of a balloon to expand the stent to a desired diameter within the vasculature. Where the stent is made of a "memory" alloy such as Nitinol, the sheath both protects the stent during delivery, and it also restrains the stent against premature deployment. Once the stent has been delivered to a desired location in the vasculature, the sheath is removed, allowing the stent to assume its natural configuration at the elevated body temperature of the patient. A balloon underlying the stent on the catheter may also be used to expand the stent for proper deployment in the vasculature.

The components of the present invention crimping tool 22 is preferably made from injection molded plastics or machined from a variety of polymers including DELRIN or TEFLON. In alternative embodiments, rubber wheels can be used. To withstand the rigors of high production rates, the present invention crimping tool can be constructed from stainless steel, brass, aluminum, or the like. Lighter metals or high strength rigid plastics can be use for portable units.

The present invention crimping tool 22 can be immersed in a fluid at a variety of temperatures or pressures, either of which is held at a steady state or is varied over time. Of course, the invention is easily adaptable to automation.

Although the exemplary embodiments described above rely on nine evenly arranged wheels to perform the crimping process, it is contemplated that fewer or more wheels can be used to sequentially or simultaneously perform the crimping process.

In yet another embodiment (not shown), an optional funnel-like clip or the like can be provided at the entrance of axial space 32 in each of the embodiments to help align and guide the stent-catheter assembly into the rotating wheels. With use of the clip, one of the user's hands is freed to perform other duties.

The present invention is sterilized and intended to be used in a cath lab by a trained technician or cardiologist. As will be appreciated by those skilled in the art, the present invention crimping tool 22 is designed both for single use applications in a cath lab by a physician, or for multiple use applications in a sterile environment in a high volume manufacturing facility. In such a manufacturing facility where sterile conditions exist, the stent crimping tool 22 can be used repeatedly to crimp stents onto balloons until the mechanism wears out. Thus, repeated uses of the present invention are contemplated for controlled, sterile environments, as are single use applications when operated by cath lab personnel.

Furthermore, the present invention crimping tool can be used with any stent that is released without a delivery system. The crimping tool may also be sold alone, because its design is robust enough to undergo many uses.

Other modifications can be made to the present invention without departing from the scope thereof. The specific dimensions, procedural steps, and materials of construction are provided as examples, and substitutes are readily contemplated which do not depart from the invention.

I claim:

1. A system for crimping a prosthesis comprising:
   a plurality of wheels, wherein:

each wheel is rotatably mounted on an axle;

each wheel has an outer circumferential surface configured to apply a radially inward force on the prosthesis;

the wheels are mounted so as to be positionable in relation to each other such that a diameter of each wheel radiates outwardly from a central axis, wherein the outer circumferential surfaces of the wheels are positionable equidistant from the axis by a first smallest possible distance to define a first space that includes the axis; and a first number out of the plurality of wheels are mounted so as to be restrained from further advancing toward the axis, thereby leaving a number of remaining wheels mounted to be capable of further advancing toward the axis, wherein the outer circumferential surfaces of the remaining wheels are positionable equidistant from the axis by a second smallest possible distance to define a second space that includes the axis, the second space being smaller than the first space.

2. The system of claim 1, wherein the plurality is nine in number.

3. The system of claim 2, wherein the first number is three in number.

4. The system of claim 1, wherein all of the axles of the plurality of wheels lie in a single common plane.

\* \* \* \* \*